United States Patent [19]

Nagpal et al.

[11] Patent Number: 5,650,279
[45] Date of Patent: Jul. 22, 1997

[54] GENE SEQUENCE INDUCED IN SKIN BY RETINOIDS

[75] Inventors: Sunil Nagpal, Irvine; Roshantha A. Chandraratna, Mission Viejo, both of Calif.

[73] Assignee: Allergan, Inc., Irvine, Calif.

[21] Appl. No.: 379,280

[22] Filed: Jan. 27, 1995

[51] Int. Cl.$^6$ .............................. C12Q 1/68; C12P 19/34; C07H 21/02; C07H 21/04
[52] U.S. Cl. .............................. 435/6; 435/91.2; 536/23.1; 536/24.3; 536/24.33
[58] Field of Search ...................... 435/6, 91.2; 536/23.1, 536/24.3–24.33

[56] References Cited

PUBLICATIONS

Breathnach, S.M. Clin Exp Immunol. 91:343–345, 1993.
Meinkoth, J. and Wahl G., Analytical Biochemistry 138:267–284, 1984.
Durand, B., et al Cell 71: 73–85, 1992.
Elder, J.T. et al J. Toxicol. Cut and Ocular Toxicol 12(2) 173–181 (1993).
Elder J.T et al J. of Investigative Dermatology 100(4):356–359, 1993.
Jackson, D.G. et al. J. of Immunology 144:2811–2815, 1990.
Kapp, A., J. of Dermatological Science 5:133–142, 1993.
Li, et al Biotechniques 16: 722–729, 1994.
Malvasi, F. et al. Immunology Today 15: 95–97, 1994.
Magelsdorf, D.J. et al. The Retinoids, Chemistry and Medicine, 2nd edition, Ed. by M.B. Sport, A.B. Roberts and D.S. Goodman Raven, Press, N.Y. 1994 pp. 319–350.
Nagpal, S. et al. Cell 70:1007–1019, 1992.

*Primary Examiner*—W. Gary Jones
*Assistant Examiner*—Dianne Rees
*Attorney, Agent, or Firm*—Knobbe Martens Olson & Bear, LLP

[57] ABSTRACT

One aspect of the invention relates to a novel human cDNA, called TIG1 (Tazarotene Induced Gene 1). Expression of the corresponding TIG1 mRNA is strongly induced from a low basal level upon treatment of skin raft cultures with the RAR β/γ selective anti-psoriatic synthetic retinoid AGN-190168 (ethyl 6-[2-(4,4) dimethyl-thiochroman-6-yl] ethynyl-nicotinate). The TIG1 mRNA is also up-regulated by AGN-190168 and the acid form AGN-190299 (6-[2-(4,4) dimethyl-thiochroman-6-yl] ethynyl-nicotinic acid) in skin raft cultures prepared from psoriatic fibroblasts and normal keratinocytes. Further, the TIG1 mRNA is similarly up-regulated by AGN-190168 in primary fibroblast and keratinocyte cultures. The low basal expression of the TIG1 mRNA is particularly advantageous when used as an indicator of retinoid action in psoriatic skin culture systems. Assay systems employing this unique TIG1 expression profile are disclosed.

18 Claims, 1 Drawing Sheet

FIG. 1

GENE SEQUENCE INDUCED IN SKIN BY RETINOIDS

FIELD OF THE INVENTION

The present invention relates generally to the field of inducible gene expression. More specifically, the invention relates to a retinoid-induced polynucleotide and assays that detect expression of this polynucleotide.

BACKGROUND OF THE INVENTION

Psoriasis is a common skin disease that reportedly afflicts as much as 3% of the population. Hyperproliferation of epidermal keratinocytes, excessive scaling of skin and infiltration of immune cells into the dermis and epidermis of affected areas distinguish this disease. Many of the features which characterize psoriatic lesions are also observed in a variety of autoimmune disorders. Like many autoimmune disorders, an underlying genetic component is thought to predispose susceptible individuals to the development of psoriasis.

Psoriatic immunopathology likely results from the activities of cytokines released by activated keratinocytes or leukocytes. Indeed, IL-1, TNF-α and IL-8 have all been implicated in disease development. The proinflammatory activity of IL-1 and its ability to induce fibroblast proliferation have been suggested to account for the cellular misregulation observed in psoriatic lesions. However, the finding that IL-1 activity in lesional psoriatic skin is actually reduced relative to either normal or uninvolved psoriatic skin argues for a different mechanism. Thus, the initiating factor responsible for the development of psoriasis may be more complex than the simple misregulation of a cytokine.

Successful management of psoriasis frequently involves the administration of immunosuppressants. Drugs used in the treatment of psoriasis include cyclosporin A, corticosteroids, methotrexate, vitamin D3, vitamin D3 analogs and retinoids. These latter compounds, for example, can both decrease keratinocyte IL-1 production and modulate the interaction between antigen presenting cells and T lymphocytes.

A topically administered synthetic retinoid has recently been shown to dramatically improve the symptoms of psoriasis. More specifically, AGN-190168 (tazarotene/ethyl 6-[2-(4,4) dimethyl-thiochroman-6-yl] ethynyl-nicotinate) is an RAR β/γ selective synthetic retinoid that has been proven effective for psoriasis treatment in phase III clinical trials.

Retinoids are the compounds comprising vitamin A and its derivatives. These chemicals play important roles in a variety of biological phenomena including: vision, hematopoiesis, bone development and pattern formation during embryogenesis. Retinoids additionally possess strong antiproliferative activities.

Retinoids exert their biological activities by binding and activating receptors that are transcription factors. These receptors are presently divided into two groups based on their ligand binding specificities. All-trans-RA (RA) binds and activates a class of retinoic acid receptors that includes RAR-α, RAR-β and RAR-γ. A different ligand, 9-cis-RA (9C-RA), binds and activates both the RARs and members of the retinoid X receptor (RXR) family. The RXR family of receptors includes RXR-α, RXR-β and RXR-γ. Thus, at least one class of retinoids exclusively binds and activates the RAR-α, RAR-β and RAR-γ receptors. This selectivity illustrates one mechanism that underlies the specificity of retinoid activity.

The number of retinoid responsive genes identified to date is very limited. Two of these genes encode cellular retinoic acid (RA) binding proteins (CRABP I and CRABP II). The CRABP I and II proteins are highly conserved across species, but are not strongly related to each other. Herein we disclose the discovery and utility of a novel retinoid induced polynucleotide.

SUMMARY OF THE INVENTION

One aspect of the present invention regards an isolated polynucleotide containing a sequence complementary to an mRNA that is induced in mammalian skin cells after treatment with ethyl 6-[2-(4,4) dimethyl-thiochroman-6-yl] ethynyl-nicotinate (AGN-190168). Significantly, this isolated polynucleotide corresponds to an mRNA that is substantially not expressed in mammalian skin cells prior to treatment with AGN-190168. Specifically, this mRNA encodes a protein that has an unmodified molecular weight of approximately 25 kDa, and has a length of approximately 1.0 kb. In one embodiment, the sequence of this polynucleotide is the complement of the sequence given by SEQ ID NO:4. Still further, this polynucleotide can be double-stranded.

A second aspect of the invention relates to a method for determining whether a test compound has potential for the treatment of psoriasis. According to the invented method, a "negative control" sample containing RNA isolated from a control culture of skin-derived cells is first obtained. The cells of this control culture have not been treated with an inducer. Next, a "test" sample containing RNA is isolated from a culture of skin-derived cells that have been treated with a test compound. The two RNA-containing samples are then hybridized with a labeled probe that has a sufficient number of consecutive nucleotides complementary to the sequence of SEQ ID NO:4 to specifically hybridize with TIG1 mRNA under high stringency conditions. These high stringency conditions can include 0.1×SSPE and 1% SDS at 65° C. The amount of hybridization between the probe and each of the samples is then quantitated. Finally, the amount of hybridization in each of samples is compared to determine if the amount of hybridization between the probe and the test sample is greater or lesser than the amount of hybridization between the probe and the negative control sample. If the amount of hybridization between the probe and the test sample is greater than the amount of hybridization between the probe and the negative control sample, than the test compound has potential in the treatment of psoriasis according to the invented method. In one embodiment of this method, the negative control sample is derived from keratinocytes or fibroblasts. In another embodiment, the probe is labeled with a radioactive label. In yet another embodiment, the amount of hybridization between the probe and the RNA samples is determined by an autoradiographic procedure.

A third aspect of the invention regards an isolated promoter that is inducible by etkyl 6-[2-(4,4) dimethyl-thiochroman-6-yl] ethynyl-nicotinate (AGN-190168). This promoter is additionally inducible by 6-[2-(4,4) dimethyl-thiochroman-6-yl] ethynyl-nicotinic acid (AGN-190299), but not by 1-(4-carboxyphenyl)-1-(7-(1,1,4,4-tetramethyl-1,2,3,4-tetrahydronaphthyl))-2-methylpropene (SR-11217) or 2-(5,6,7,8-tetrahydro-5,5,8,8-tetramethyl naphthalen-2-yl)-2-(4-carboxyphenyl)-1,3-dioxolane (SR-11237). More particularly, the promoter directs expression of the TIG1 mRNA in normal human cells.

DETAILED DESCRIPTION OF THE INVENTION

Overview

We disclose the sequence and utility of a novel retinoid inducible polynucleotide. Expression of this polynucleotide at the mRNA level is dramatically up-regulated by treatment of skin cells with the synthetic retinoid, AGN-190168. Advantageously, expression of this polynucleotide, called TIG1, is barely detectable in resting cells. This profile of gene expression has been exploited in sensitive assays for detecting compounds having retinoid activity in psoriatic skin cells.

Introduction

Procedures to identify candidate compounds for the treatment of psoriasis rely on sensitive assays that detect transformations in psoriatic tissue. Such assays can, for example, detect alterations at the level of gene expression. An assay of this type may detect the expression of a gene that is up-regulated in psoriatic cells upon exposure to known therapeutic compounds. Such assays provide correlative evidence that both a test compound and a compound of known therapeutic value have similar effects on the expression of particular genes. Thus, test compounds that stimulate TIG1 expression can be identified as having potential as therapeutic drugs.

Although CRABP II is regarded as a marker for retinoid action in normal skin, this gene is highly up-regulated in lesional psoriatic skin (Didierjean et al., *Biochem. Biophys. Res. Commun.* 180:204 (1991)). This high level of basal activity complicates the detection of small increases in gene expression, as might be caused by the action of a therapeutic drug. A small increase, measured against a high level of background gene expression, could easily be rendered undetectable. Conversely, the same small increase in gene expression would more easily be measured by employing a probe that detected an mRNA having a low basal expression. Thus, an assay for inducible gene expression based on the detection of an mRNA that had a low basal expression would clearly benefit from a favorable signal-to-noise ratio. Such an assay would advantageously be highly sensitive to small increases in gene expression. Thus, the high basal expression of the CRABP II mRNA can be regarded as a disadvantage when CRABP II is employed as an indicator of retinoid activity in psoriatic tissue.

Conceivably, the high basal expression of the CRABP II mRNA in cells derived from psoriatic tissue could result from the presence of a cis-regulatory promoter motif that was independent of the RA-responsive element. We reasoned that such an element could have constitutive enhancer-like activity in psoriatic cells. We therefore set out to identify gene sequences that were induced by retinoids, but that were not subject to high levels of basal expression in psoriatic tissue. In particular, we sought to isolate gene sequences that were expressed at low levels in psoriatic skin cultures, and that were highly up-regulated following treatment with a retinoid that is known to improve psoriasis symptoms.

As a result of this work, we have identified a novel retinoid-inducible cDNA, called TIG1, that has definite advantages over the CRABP II cDNA when used as a probe in assays for retinoid activity. The TIG1 mRNA was found to be up-regulated by AGN-190168 in both normal and psoriatic skin raft cultures as well as in primary keratinocyte and fibroblast cultures. Further, we discovered that TIG1 mRNA expression was up-regulated in the AGN-190168 treated psoriatic lesions of patients but was expressed only very weakly in non-lesional psoriatic skin and lesional psoriatic skin in the absence of treatment. Assays for retinoid derivatives that induce the TIG1 mRNA provide a means for identifying compounds that can be further investigated as candidates for the treatment of a wide variety of retinoid responsive diseases.

One aspect of the present invention regards assays that can identify compounds having "bioactivity." As used herein, the term "bioactivity" refers to the ability of a chemical compound to affect an observable change in a biological system. In this context the synthetic retinoid AGN-190168 is an example of a drug that exhibits bioactivity in assays encompassed by the present invention. In particular, AGN-190168 stimulates expression of the novel gene, TIG1. Since this activity can be detected as increased expression of the TIG1 mRNA, AGN-190168 is said to exhibit bioactivity. Drugs that fail to induce the TIG1 mRNA would be said to exhibit no bioactivity in this assay system.

In addition to nucleic acid-based assays and expression assays, we contemplate immunological assays that employ anti-TIG1 antibodies as reagents for identifying bioactive retinoids. In this regard, we contemplate the production of anti-TIG1 antibodies for use as reagents in the detection of TIG1 protein. More specifically, we contemplate that all or part of the TIG1 cDNA disclosed herein can be operationally ligated to procaryotic or eukaryctic expression or gene fusion vectors and introduced into living cells. The proteins encoded by these vectors can be used as immunogens to elicit the production of TIG1-specific antibodies. One advantage of using fusion proteins as immunogens derives from the fact that fusion proteins can be partly purified more easily than native proteins. Fusion proteins appropriate for the production of TIG1 immunogens can be any fusion protein familiar to one having ordinary skill in the art. Such fusion proteins can, for example, comprise glutathione S-transferase (GST) protein sequences as encoded by vectors that are available from Pharmacia (Piscataway, N.J.). Other vectors appropriate for the production of TIG1 immunogens can direct the expression of TIG1-protein A fusion proteins or fusion proteins having metal-binding domains or epitopes recognized by commercially available antibodies.

According to an alternative strategy for the production of anti-TIG1 antibodies, synthetic peptides predicted to represent antigenic regions of the TIG1 protein can be employed as immunogens. For example, these synthetic peptides can be coupled to carriers such as keyhole limpet hemocyanin (KLH) with MBS (Pierce, Rockford, Ill.) and used as immunogens for the production of anti-TIG1 antiserum. Antibodies produced in this fashion can be used to detect the TIG1 protein by cell staining, immunoprecipitation and Western blotting protocols. Anti-TIG1 antibodies can be used as reagents for detecting the induction of TIG1 proteins by retinoids that include AGN-190168, and other compounds having potential as therapeutics in the treatment of psoriasis.

Among the types of diseases contemplated as therapeutic targets of retinoids that induce TIG1 are: psoriasis, acne, dysplasias, cancers and autoimmune diseases. The category of contemplated dysplasias includes precancerous lesions of the epithelial tissues such as oral leukoplakias, dysplasia of the cervix, larynx and bronchi. The category of contemplated cancers includes carcinomas of the skin, head and neck, cervix, uterus, breast and prostate. The category of contemplated autoimmune diseases includes rheumatoid arthritis, osteoarthritis, systemic lupus erythematosus, pemphigus vulgaris and pemphigus foliaceous. Synthetic retinoids may also be therapeutically effective for the treatment of atopic dermatitis, allergic rhinitis and asthma.

The discoveries that led to the present invention began with the isolation of gene sequences that were regulated by retinoids in normal skin raft cultures. Inducibility of the mRNAs corresponding to these isolates was verified by Northern analysis. The range of inducibility of the cloned cDNA in a variety of skin-derived cell types was investigated and the findings compared with results obtained using cells of psoriatic origin. Finally, we demonstrated how the novel polynucleotides described herein can be used in a highly sensitive assay for retinoids that affect gene expression in psoriatic skin cultures. As described above, compounds identified according to this assay will be candidates for the treatment of psoriasis and other retinoid responsive diseases.

Although other materials and methods similar or equivalent to those described herein can be used in the practice or testing of the present invention, the preferred methods and materials are now described. General references for methods that can be used to perform the various nucleic acid manipulations and procedures described herein can be found in *Molecular Cloning: A Laboratory Manual* (Sambrook et al. eds. Cold Spring Harbor Lab Publ. 1989) and *Current Protocols in Molecular Biology* (Ausubel et al. eds., Greene Publishing Associates and Wiley-Interscience 1987). The disclosures contained in these references are hereby incorporated by reference. A description of the experiments and results that led to the creation of the present invention follows.

A variety of skin-derived cell types were employed in the development and practice of the present invention. The cells employed in these procedures served as sources of RNA that were used both for the construction of a cDNA library and for the analysis of retinoid-regulated gene expression.

Example 1 describes the methods used to obtain non-transformed human keratinocytes and fibroblasts. RNA isolated from these cells was subsequently used in gene expression studies.

EXAMPLE 1

Establishment of Primary Cell Cultures of Human Keratinocytes and Fibroblasts

Fresh human foreskins were washed in ethanol (70%) for 10 seconds followed by two washings in keratinocyte growth medium (KGM) purchased from Clonetics (San Diego, Calif.). Tissue samples were cut into small pieces (4 mm diameter) and incubated with trypsin (0.05% GIBCO-BRL, Grand Island, N.Y.) for 24 hours at 4° C. After digestion, the epidermis that contained keratinocytes was removed and dissociated into a cell suspension using sterile forceps. Keratinocytes were pelleted at 1000×g in a Beckman model TJ-6 centrifuge for 6 minutes at 4° C. The resulting cell pellet was then resuspended in KGM and filtered through a 100 micron nylon mesh membrane from Tetko, Inc. (New York, N.Y.). The filtrate, which contained keratinocytes, was cultured in a T75 tissue culture flask with 20 ml of KGM containing 10% fetal bovine serum (FBS). After three days the culture medium was replaced with KGM that did not contain FBS. Keratinocytes were maintained in serum-free media and split at 80% confluency for four passages prior to retinoid treatment.

Fibroblasts were isolated by first cutting the remaining dermis from the foreskins into small pieces using a scalpel, and then incubating with Hanks' buffer containing collagenase (0.1% for 1 hour at 37° C.). The digest was filtered through a nylon mesh and centrifuged as before. Fibroblasts were resuspended in 20 ml DMEM containing 10% FBS in a T75 tissue culture flask. Cells were maintained in DMEM with FBS, split at 80% confluency and used for procedures involving treatment with retinoids after 2–3 passages.

In addition to the keratinocyte and fibroblast cultures prepared as described above, three-dimensional reconstructed "skin raft cultures" were also used in procedures involving retinoid induction and RNA isolation. Normal skin raft cultures, which are alternatively called "organotypic" or "skin equivalent" cultures, can be commercially obtained. The normal skin raft cultures employed in the procedures described herein were purchased from Advanced Tissue Sciences (La Jolla, Calif.).

The structural relationships among the cellular and acellular components comprising these cultures advantageously reproduce some of the complex features which characterize skin. In particular, skin raft cultures represent three-dimensional biological models having dermal, epidermal and corneal layers. In the production of these cultures, neonatal fibroblasts were seeded onto an inert nylon mesh and grown into a dermal tissue. Keratinocytes seeded atop this dermal layer gave rise to an epidermis.

In addition to normal skin raft cultures, we also employed skin raft cultures prepared from psoriatic fibroblasts and normal human keratinocytes. These "psoriatic skin raft cultures" were perturbed in their epidermal morphology when compared to their normal counterparts. Thus, these cultures advantageously retained at least some of the pathologic features which characterized the condition of the fibroblast donor.

Example 2 describes the method used to prepare psoriatic skin raft cultures.

EXAMPLE 2

Preparation of Skin Raft Cultures Containing Psoriatic Fibroblasts

Human cultured psoriatic fibroblasts ($2 \times 10^5$ cells) obtained from lesional punch biopsies were mixed with type I collagen (3.5 mg/ml, Collaborative Biochemical Products, Bedford, Mass.), neutralized with NaOH (1N) and plated in 24-well tissue culture plates. Human primary foreskin keratinocytes ($5 \times 10^5$ cells/well) were layered on top of the collagen layer after 24 hours. The collagen gels containing fibroblasts and keratinocytes were raised to the air-liquid interface after 24 hours according to the procedure described by Bell et. al. in *Proc. Natl. Acad. Sci. USA* 76:1274 (1979). Rafts were maintained in FAD medium supplemented with FBS (10%), hydrocortisone (400 ng/ml), cholera toxin ($10^{-10}$M, Sigma), epidermal growth factor (10 ng/ml), fungibact (1%), adenine (0.089 mM), and insulin (0.105 IU/ml), as described by Duvic et. al. in *J. Invest. Dermatol.* 102:462 (1994). The psoriatic rafts were grown for 10 days and used for experiments on Day 11. We note that FAD medium contains 675 ml DMEM (Sigma), 225 ml nutrient Fixture F-12 Ham (Sigma), 16.38 mg adenine and 4.5 mg insulin.

An important aspect of the in vitro procedures described below involved the induction of cultured cells with retinoids. Although the following Example illustrates how keratinocytes, fibroblasts and skin raft cultures can be induced with AGN-190168, similar procedures can be used to induce cultured cells with other retinoid compounds. We also anticipate that combinations or mixtures of agents can be used according to this protocol. Such combinations could for example, include retinoid agonists and antagonists.

Example 3 describes the methods used to induce skin-derived cell cultures with retinoids.

EXAMPLE 3

Retinoid Treatment of Cultured Cells

Keratinocyte and fibroblast cultures (80% confluency) were respectively maintained overnight in KGM and DMEM, containing charcoal-treated FBS (10%) before treatment with AGN-190168 (1 µM for 24 hours). On Day 0, skin raft cultures were kept overnight in serum free maintenance medium and then either mock-treated or treated with AGN-190168 (1 µM) on Day 1 and Day 3. Cultures were harvested on Day 4 by directly immersing them in guanidine thiocyanate solution for total RNA preparation. Similarly, psoriatic skin raft cultures were treated with AGN-190168 (1 µM each) on Day 1 and Day 3 before harvesting on Day 4.

The subtraction hybridization procedure described by Li, et al. in *BioTechniques* 16:722 (1994) was used to isolate AGN-190168 regulated gene sequences from normal skin raft cultures. These procedures ultimately led to the identification of a cloned cDNA sequence whose corresponding mRNA was dramatically induced by retinoid treatment.

Example 4 describes the methods used to construct a cDNA library enriched for sequences induced by the retinoid AGN-190168.

EXAMPLE 4

Construction of a cDNA Library Enriched for Gene Sequences Induced in Skin Raft Cultures by AGN-190168

Total RNA was prepared from mock-treated and AGN-190168 treated skin raft cultures by the guanidine thiocyanate procedure using materials purchased from Promega (Madison, Wis.). Poly(A)+ RNA was purified with oligo-dT cellulose purchased from Pharmacia (Piscataway, N.J.) and used according to manufacturer's instructions. Directional cDNA was synthesized using an oligo $(dT)_{15}$-Not I primer purchased from GIBCO-BRL (Gaithersburg, Md.) in a standard reverse transcription protocol. The resulting cDNA was ligated to SalI adapters and double-digested with NotI and SalI restriction endonucleases. The digested cDNA harbored a NotI site at the 3' terminus and SalI site at the 5' terminus. The cDNA was then ligated between the SalI and NotI sites of the pSPORT-1 vector (GIBCO-BRL) and electroporated into electroMAX DH12S bacterial host cells (GIBCO-BRL). Single-stranded (ss) DNA was prepared from $1 \times 10^6$ pSPORT-1 transformants using the M13K07 helper phage ($>1 \times 10^{11}$ pfu/ml,GIBCO-BRL).

A second directional cDNA library was similarly constructed between the SalI and NotI sites of the pSPORT-2 vector (GIBCO-BRL) using cDNA prepared from a mock-treated skin raft culture essentially as described above. The ligated cDNA library was electroporated into DH12S cells. Double stranded (ds) plasmid DNA was prepared from $1 \times 10^6$ transformants. The pSPORT-2 plasmid cDNA library was linearized with SalI and in vitro transcribed using T7 RNA polymerase (GIBCO-BRL) in the presence of 2 mM biotin-14-CTP also as described by Li et al. in *BioTechniques* 16:722 (1994).

Biotinylated driver RNA was further treated with RNase-free DNase I, passed through a Sepharose S-300 column (Pharmacia), ethanol precipitated and resuspended in TE. The poly(A)+ region of pSPORT-1 ssDNA was blocked with a NotI-oligo primer having the sequence 5'-GCGGCCGCCCT$_{15}$-3' (SEQ ID NO:1) by incubating at 70° C. for 20 minutes with 600 µM dTTP and Taq DNA polymerase. Poly dA blocked ssDNA (600 ng) was hybridized with biotinylated RNA (80 µg) in 25 µl of 2× hybridization buffer (80% formamide, 100 mM HEPES (pH 7.5), 2 mM EDTA and 0.2% SDS) for 24 hours at 42° C. with shaking (200 rpm). The control experiment contained all the above components except biotinylated RNA. Following the hybridization reaction, streptavidin (Promega) was added to a final concentration of 5 µg/µl, and the mixture incubated at room temperature for 5 minutes. Common ssDNA-RNA sequences hybridized with biotin-streptavidin complexes were removed by phenol: chloroform: isoamyl alcohol (25:24:1) extraction. The streptavidin extraction procedure was repeated 5 times. Nonhybridized ssDNA was precipitated, pelleted, and dissolved in 10 µl of water. A 2 µl aliquot of the DNA solution was electroporated into DH12S host cells.

While control ssDNA (600 ng) yielded 1.45 million colonies, only about 18,000 colonies were obtained after the subtraction procedure.

Example 5 describes the methods used to identify cDNA clones corresponding to mRNAs whose expression are influenced by retinoids.

EXAMPLE 5

Screening of Subtracted cDNA Clones by Southern Hybridization

Purified DNA obtained from transformants in the subtraction library was double-digested with SalI and NotI restriction endonucleases, electrophoresed in duplicate, transferred to nytran membranes for Southern hybridization and probed with random primed $^{32}$P-labeled cDNA obtained from either mock-treated or AGN-190168 treated normal skin raft cultures. Random priming was carried out using reagents that had been purchased as a kit from Amersham (Arlington Heights, Ill.). Probes were hybridized overnight at 42° C. in 6× SSPE, 5× Denhardt's reagent, 0.5% SDS, 10 µg/ml denatured salmon sperm DNA and 50% formamide (pH 7.4). Membranes were washed under high stringency conditions (0.1×SSPE/1% SDS) at 65° C. for 45 minutes before exposure to X-ray film.

Southern analysis indicated that the inserts in subtracted cDNA clones #B27 and #B16 hybridized the heterogeneous probe generated from RNA of the induced cell population more intensively than the control probe. This result indicated clones #B27 and #B16 corresponded to AGN-190168 induced mRNAs.

As described below, induction of the mRNAs corresponding to cDNA clones #B27 and #B16 was confirmed by Northern analysis of total RNA isolated from mock-treated and AGN- 190168 treated skin raft cultures. The blot was also probed with labeled GAPDH cDNA to ensure that equal quantities of control and retinoid treated RNA were used in the Northern analysis.

Example 6 describes the methods used to verify inducibility of the #B27 and #B16 cDNA isolates and determine the size of the corresponding mRNA transcripts.

EXAMPLE 6

Confirmation of mRNA Inducibility by Northern Analysis

Total RNA (10 µg) isolated from mock-treated or AGN-190168-treated normal skin raft cultures was electrophoresed on 1% agarose, 1.1M formaldehyde gels, transferred to nytran membranes and probed with either $^{32}$P-labeled #B27,

B16 or GAPDH cDNAs according to standard laboratory procedures. Individual Northern blots having one lane each of the control and AGN-190168 induced skin raft culture RNA were hybridized with the radiolabeled probes overnight at 42° C. in 50% formamide, 5× SSPE, 1× Denhardt's reagent and 0.2 mg/ml denatured salmon sperm DNA. The membranes were subsequently washed under high stringency conditions (0.1×SSPE/1% SDS) at 65° C. for 30 minutes before exposure to X-ray film.

Autoradiographic results confirmed that mRNAs corresponding to the #B27 and #B16 cDNA clones were induced by AGN-190168 treatment. The GAPDH probe hybridized a unique 1.8 kb mRNA with similar intensities in lanes corresponding to control and induced cell RNAs. This verified that similar RNA masses had been loaded in each of the lanes of the Northern blot. Both the #B27 and the #B16 probes hybridized to AGN-190168 induced mRNAs of 1.0 kb in length. Inducibility of these mRNAs was evidenced by exceedingly weak or undetectable hybridization to control cell RNA and intense hybridization to RNA isolated from AGN-190168-treated skin raft cultures. These findings suggested the two cDNA probes hybridized the same mRNA species.

Interestingly, when normal skin raft cultures were treated with AGN-192620 (an RXR-specific retinoid), mRNA expression of #B27 and #B16 was unchanged when compared with the mock-treated control. Thus, these mRNAs were induced by an RAR-specific, but not by an RXR-specific, retinoid.

The results presented above also demonstrated that blot hybridization protocols can be used to detect induced expression of the #B27 and #B16 mRNAs under high stringency conditions (i.e. 0.1×SSPE/1% SDS at 65° C.). More specifically, the fact that single AGN-190168 induced mRNA species were detected in the Northern blotting procedure indicated that other hybridization protocols, for example based on dot or slot blotting techniques, would also have utility in detecting expression of these mRNAs.

The DNA sequences of the cloned AGN-190168 induced polynucleotides were next determined and analyzed. As described in the following Example, a computer-assisted search of the nucleic acid and protein sequence databases indicated that the two inducible clones represented different isolates of the same previously unknown gene product. Interestingly, the hydropathic profile of the protein encoded by the retinoid induced clone was found to be similar to the product of another retinoid inducible gene expressed in cells of the immune system.

Example 7 describes the nucleic acid and protein sequence analyses used to assess the novelty and possible function of the retinoid inducible gene products isolated as above.

EXAMPLE 7

Analysis of the Predicted Protein Encoded by the TIG1 (#B27/#B16) cDNA

Nucleotide sequencing of the #B27 and #B16 cDNAs was performed by SEQUATECH (Mountain View, Calif.) according to a dideoxy chain termination protocol using SP6 and T7 sequencing primers. Comparison of the results indicated that clones #B27 and #B16 contained identical inserts. Hereafter, the AGN-190168 induced polynucleotide isolated according to the foregoing procedure is referred as "TIG1" (Tazarotene Induced Gene 1). The polynucleotide sequence corresponding to the sense strand of the TIG1 ds-cDNA (SEQ ID NO:4) and the hypothetical translation (SEQ ID NO:5) of the longest open reading frame are presented in the sequence listing. Polynucleotides having sequences complementary to the sense strand of the sequence presented as SEQ ID NO:4 will be capable of specifically hybridizing the single-stranded TIG1 mRNA. The TIG1 cDNA sequence spanned 862 base pairs (bp), contained an open reading frame that extended from position 37 to 720 bp and was predicted to encode a protein having 228 amino acids with an unmodified molecular weight of approximately 25 kDa. The TIG1 cDNA had a poly(A) addition signal sequence (5'-AATAAA-3') located at position 826 bp.

Polynucleotide and protein sequence analyses were conducted using the MacDNASIS (Hitachi, San Bruno, Calif.) software package. Homology searches from DNA (GenBank and EMBL) and protein (Swiss-Prot) databases failed to identify any known DNA or protein sequence that was identical to the TIG1 nucleic acid or predicted amino acid sequence. These results indicated that TIG1 represented a novel cDNA isolate.

The predicted protein encoded by the TIG1 cDNA contained a hydrophobic stretch of 19 amino acids (amino acids 16 to 34) and a glycosylation signal (NVT, amino acids 142 to 144) sequence. These features suggested that the TIG1 cDNA encoded a transmembrane protein with an extracellular region of 194 amino acids, a membrane spanning domain of 19 amino acids and a cytoplasmic tail region of 15 amino acids.

Figure 1:
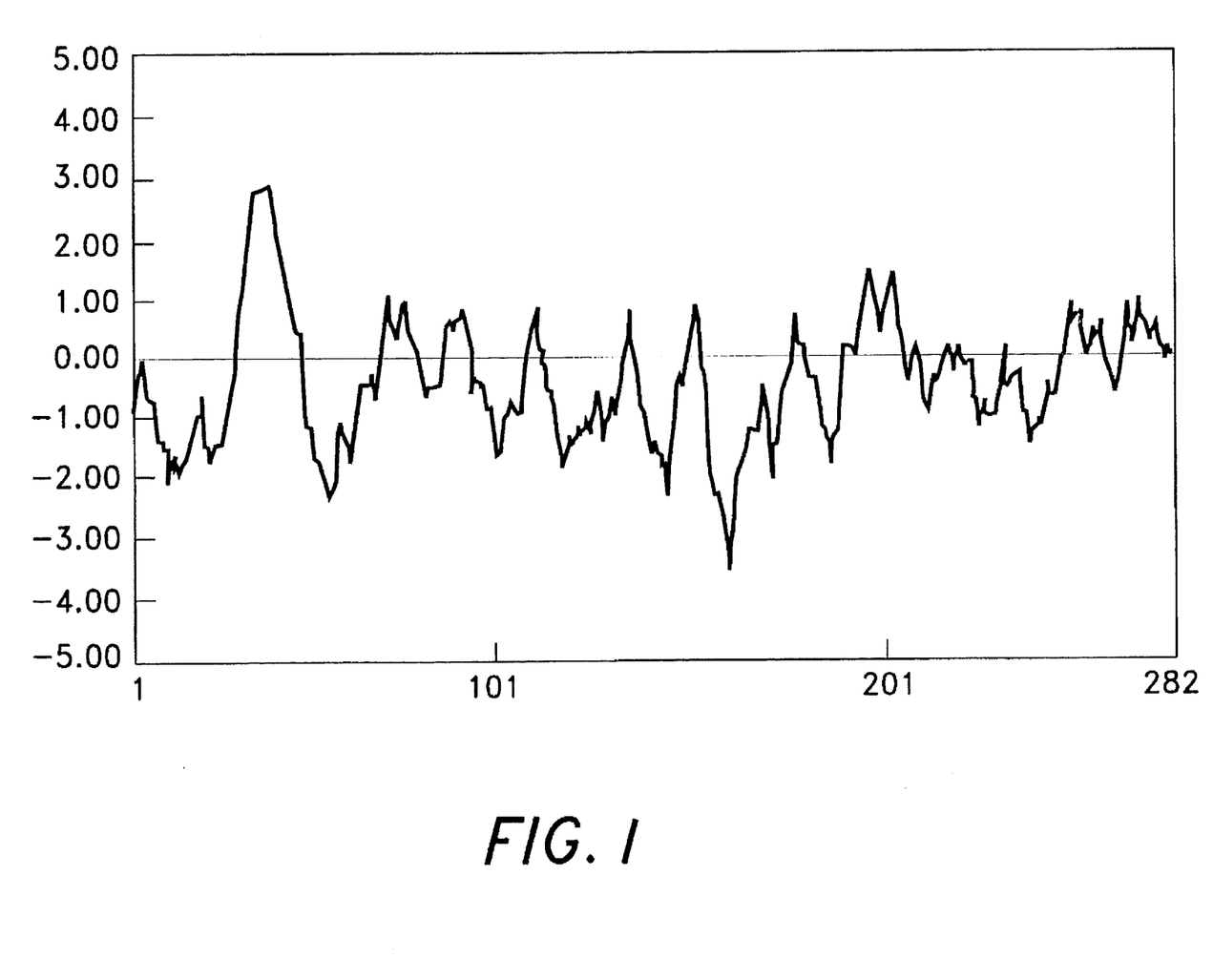
FIG. 1 shows a Kyte-Doolittle hydrophobicity plot for the predicted TIG1 polypeptide.

A Kyte-Doolittle hydropathic profile of TIG1 (FIG. 1) resembled that of CD38 (Jackson and Bell *J. Immunol.* 144:2811 (1990)), a retinoid-responsive gene expressed in cells of the immune system (Malavasi et al. *Immunology Today* 15:95 (1994)). The Y-axis of the plot shown in FIG. 1 represents hydrophobicity while the X-axis represents amino acid position. Regions of the protein having hydrophobicity values greater than +0.50 were predicted to be membrane-embedded according to the analysis conducted using the MacDNASIS program. Like the predicted TIG1 protein, CD38 has a short cytoplasmic tail region (21 amino acids), a single transmembrane domain and a long extracellular region. Thus, the similarities between the TIG1 and CD38 hydropathic profiles suggested that TIG1 possessed structural features characteristic of other proteins that localize to the cell surface.

We next investigated whether inducibility of the TIG1 mRNA extended to psoriatic skin raft cultures. Saiag et al. (*Science* 230:669 (1985)) previously demonstrated that psoriatic fibroblasts induced hyperproliferation of normal keratinocytes in skin raft cultures in vitro. Therefore, psoriatic skin raft cultures prepared from psoriatic lesional fibroblasts and normal keratinocytes were either mock-treated or treated with AGN-190168 to investigate inducibility of TIG1 in the context of the psoriatic phenotype.

Example 8 describes the methods used to demonstrate inducible expression of TIG1 mRNA in psoriatic skin raft cultures.

EXAMPLE 8

Induction of the TIG1 mRNA in Psoriatic Skin Raft Cultures

Total RNA (10 μg) isolated from mock-treated or AGN-190168 treated psoriatic skin raft cultures was electrophoresed on a 1% agarose, 1.1M formaldehyde gel, transferred to a nytran membrane and probed with $^{32}$P-labeled TIG1 or GAPDH cDNAs according to standard procedures. The membrane was hybridized with radiolabeled probes overnight at 42° C. in 50% formamide, 5× SSPE, 1× Denhardt's reagent and 0.2 mg/ml denatured salmon sperm DNA. The hybridized membrane was washed under high stringency conditions (0.1×SSPE/1% SDS) at 65° C. for 30 minutes before exposure to X-ray film.

Autoradiographic results indicated that AGN-190168 induced the TIG1 mRNA in psoriatic skin raft cultures. The uniform signal intensity of the 1.8 kb GAPDH band in lanes of RNA from mock-treated and AGN-190168 treated psoriatic skin rafts confirmed equivalent RNA loathing. Significantly, the lane on the Northern blot corresponding to RNA isolated from the mock-treated psoriatic skin raft had no detectable hybridization signal corresponding to the TIG1 mRNA. Thus, we found no evidence for TIG1 expression in untreated psoriatic skin raft cultures. Conversely, treatment with AGN-190168 led to a strong TIG1 hybridization signal at roughly 1.0 kb. Expression of the TIG1 mRNA represented a sensitive indicator for AGN-190168 bioactivity in this experimental system.

Expression of TIG1 mRNA in psoriatic lesions of patients who were topically administered with AGN-190168 was also investigated to establish a correspondence between the in vitro results described above and the in vivo induction of the TIG1 gene product.

Example 9 describes the methods used to demonstrate that in vitro induction of the TIG1 mRNA by AGN-190168 recapitulated the in vivo activity of this retinoid in psoriatic lesions.

EXAMPLE 9

Topical Application of AGN-190168 Induced TIG1 mRNA Expression in Skin of Psoriasis Sufferers Psoriatic lesions of patients were topically administered with 0.05% AGN-190168 cream twice daily for a period of four weeks. Skin punch biopsies were taken on day 0 (before the start of treatment), day 3 (after three day application of AGN-190168) and day 15 (after two weeks of AGN-190168 administration). In situ hybridization using TIG1 antisense RNA labeled with digoxigenin using materials purchased as a kit from Boehringer Mannheim (Indianapolis, Ind.) showed no evidence for TIG1 mRNA expression in either non-lesional psoriatic skin or in day 0 lesional skin biopsies. In contrast, TIG1 mRNA expression was readily detected at day 3 and/or day 14 in suprabasal epidermal keratinocytes of psoriatic lesional biopsies that had been treated with AGN-190168. Patients who therapeutically responded to AGN-190168 treatment after four weeks of application showed an up-regulation of TIG1 mRNA in day 3 and/or day 14 biopsies.

Thus, the induction of TIG1 mRNA by AGN-190168 was observed in two and three dimensional cultures of keratinocytes and fibroblasts as well as in the epidermis of psoriatic patients treated with AGN-190168. Although TIG1 was induced by AGN-190168 in cultured primary fibroblasts and in vivo in psoriatic lesional skin, in situ hybridization experiments indicated that TIG1 was expressed after AGN-190168 treatment only in suprabasal epidermal keratinocytes but not in the dermal fibroblasts.

The experimental results presented above established the correspondence between retinoids that induced TIG1 mRNA expression in vitro and in vivo. Thus, we believe that inducible TIG1 mRNA expression advantageously serves as a reliable indicator of retinoid bioactivity in assays that can be carried out in both in vitro and in vivo experimental systems.

The TIG1 mRNA represents only the second polynucleotide that is known to be induced in skin by retinoids. The other inducible polynucleotide, CRABP II, is however constitutively expressed in psoriatic tissue. In contrast, the TIG1 mRNA is only very weakly expressed in resting cells of psoriatic origin, and as described below is induced by multiple RAR-specific ligands. TIG1 is not induced by any of the RXR ligands tested to date. Thus, TIG1 is the only gene known to be preferentially induced in skin by RAR-specific ligands. Significantly, RAR-specific ligands are therapeutically important as anti-psoriatic agents. Therefore, the TIG1 probe can advantageously be employed as an indicator of RAR ligand bioactivity in the search for novel therapeutics. Thus, we proceeded to develop assays based on the detection of induced TIG1 mRNA for identification of candidate retinoid therapeutic agents. Retinoid derivatives that induce TIG1 gene expression are likely to employ signal transduction mechanisms similar or identical to that employed by AGN-190168.

Contemplated assays for the induction of TIG1 expression can detect the TIG1 mRNA by any of a number of procedures familiar to those having ordinary skill in the art. For example, contemplated assays can detect the TIG1 mRNA by hybridization protocols such as those disclosed by Meinkoth et al., in *Analytical Biochemistry* 138:267 (1984), the disclosure of which is hereby incorporated by reference. These hybridization protocols include detection of the TIG1 mRNA in a population of immobilized cellular RNA, or alternatively detection of the TIG1 mRNA in a sandwich hybridization protocol. In the latter procedure, an unlabeled probe is affixed to a solid support and serves as a capture probe that hybridizes one region of the TIG1 mRNA. A labeled nucleic acid probe can bind a different region of the TIG1 mRNA in a detection step.

In addition to the hybridization techniques described above, those of ordinary skill in the art will recognize that a large number of other methods of TIG1 mRNA detection will be useful in assays for identifying test compounds for the treatment of psoriasis. For example, induction of the TIG1 mRNA can be detected and quantitated by techniques including S1 assays, RNase protection assays and primer extension assays. Those having ordinary skill in the art will be acquainted with the features and utilities of these assays as they relate to RNA detection. General descriptions of these techniques can be found in *Molecular Cloning: A Laboratory Manual* (Sambrook et al. ads. Cold Spring Harbor Lab Publ. 1989) and *Current Protocols in Molecular Biology* (Ausubel et al. ads., Greene Publishing Associates and Wiley-Interscience 1987) on pages 7.58–7.83.

In S1 and RNase protection assays, the TIG1 mRNA is quantitated by hybridizing RNA samples isolated from cells that are uninduced or induced with a retinoid such as AGN-190168 with labeled nucleic acid probes harboring sequences complementary to the TIG1 mRNA. If TIG1 mRNA is present in the sample, that mRNA will hybridize to the labeled, complementary nucleic acid strand to form a double-stranded molecule in the region corresponding to the complementary portion of the probe. Regions of the probe that are not complementary to the TIG1 mRNA will remain single-stranded. If the probe is a DNA probe, unhybridized probe and single-stranded regions of hybridized probe can be digested with S1 nuclease. If the probe is an RNA probe, unhybridized probe and single-stranded regions of hybridized probe can be digested with RNase. The protected length of the probe, visualized by autoradiography of digest products that have been electrophoretically separated, will be diagnostic of the presence of TIG1 mRNA. When the hybridization procedure is carried out in probe excess, quantitative results can be obtained to indicate the presence of TIG1 mRNA in the starting sample.

In contemplated primer extension assays, an end-labeled oligonucleotide primer which is complementary to a segment of the TIG1 mRNA is hybridized with samples of RNA isolated from cells that are either uninduced or induced with a retinoid such as AGN-190168. If the TIG1 mRNA is present in the sample, the oligonucleotide primer will hybridize to the complementary portion of the TIG1 mRNA. The primer can then be extended to the 5' end of the mRNA by the activity of a reverse transcriptase using the TIG1 mRNA as a template for DNA synthesis. An extension product of the appropriate size, detected on an autoradiograph of electrophoretically separated extension products, will indicate the presence of TIG1 mRNA in the starting population of RNA.

Labels for nucleic acid hybridization probes of the present invention can be any label appropriate for DNA or RNA probes. Such nucleic acid labels can be radioactive or non-radioactive. Non-radioactive labels can be detected by a visible color change or by the emission of light of sufficient intensity that photographic or X-ray film can be exposed.

The following Example illustrates how blot hybridization protocols can be used to identify compounds having bioactivity similar to AGN-190168. In this procedure, AGN-190168 is used as a positive control for compounds that induce TIG1 expression. Mock-induction of the same cultured cell type is used as the negative control in this procedure.

In the practice of the method described below, determination of retinoid bioactivity is based on the ability of test compounds to induce TIG1 mRNA expression above the level of basal expression detected in RNA samples isolated from untreated control cells. Accordingly, if an RNA sample isolated from cells treated with a test compound does not contain proportionately more TIG1 mRNA than a sample isolated from untreated control cells, then that test compound will be judged to have no bioactivity. Thus, RNA samples isolated from untreated control cells or cells treated with a compound that does not induce TIG1 mRNA expression serves as a baseline for measuring inducible expression. Compounds having bioactivity similar to that of AGN-190168 are identified by comparing expression of TIG1 mRNA in cells treated with test compounds and cells treated with AGN-190168 as a positive control for TIG1 mRNA induction.

As described below, the invented assay has been used to prove that at least one RAR-specific retinoid, in addition to AGN-190168, induced TIG1 mRNA expression in psoriatic skin raft cultures. This RAR-specific retinoid is a candidate for psoriasis treatment according to the method of the present invention. In contrast, compounds that do not substantially induce TIG1 mRNA expression above the basal level observed in untreated cells would not be considered for further evaluation as psoriasis treatments according to the invented method.

Example 10 describes a blot hybridization assay for identifying compounds that induce TIG1 mRNA expression in psoriatic skin raft cultures. Skin-derived keratinocytes, fibroblasts and normal skin raft cultures can be substituted for the psoriatic skin raft cultures of the following procedure with equally good results. However, the advantages underlying use of the TIG1 probe as an indicator of retinoid bioactivity are particularly evident in systems exhibiting the psoriatic phenotype.

EXAMPLE 10

Hybridization Assay for Induction of the TIG1 mRNA by Retinoids

Psoriatic skin raft cultures were propagated under standard conditions. Parallel cultures were mock-treated or induced with 1 µM concentrations of various retinoid compounds to be tested for bioactivity. A mock-treated culture was used as a negative control to establish basal level expression of TIG1 mRNA. The RAR-specific ligand AGN-190168 was used as a positive control for TIG1 induction. The RAR-specific ligand, AGN-190299 (6-[2-(4,4) dimethyl-thiochroman-6-yl] ethynyl-nicotinic acid), was used as a test compound in this procedure. Cultures were induced according to the procedure described under Example 3 and total RNA was isolated by the procedure of Example 4. RNA (10 µg) from each of the three samples was separated by electrophoresis on 1% agarose, 1.1M formaldehyde gels, transferred to nytran membranes and probed with $^{32}$P-labeled TIG1 cDNA probe. The same blots were simultaneously probed with $^{32}$P-labeled GAPDH cDNA probes (Clonetech, Palo Alto, Calif.). Hybridization was carried out in 50% formamide, 5× SSPE, 1× Denhardt's reagent and 0.2 mg/ml denatured salmon sperm DNA at 42° C. overnight. The blots were subsequently washed under high stringency conditions in 0.1×SSPE/1% SDS. Blots were then exposed to X-ray film. Upon developing the autoradiographs, similar intensities of the GAPDH hybridization signals in all lanes confirmed uniform RNA loading. Relative intensities of the TIG1 bands served as direct indicators of retinoid bioactivity.

Results from the TIG1 Northern hybridization confirmed the low constitutive expression and strong inducibility of this mRNA in psoriatic skin raft cultures. No detectable TIG1 signal was present in the untreated control lane. RNA isolated from the culture induced with AGN-190168 gave a strong TIG1 mRNA signal at 1.0 kb as expected. A band of similar size and slightly greater intensity was observed in the lane corresponding to RNA from the AGN-190299 induced culture. These results indicated that AGN-190299 was strongly bioactive in the TIG1 induction assay. Thus, AGN-190299 was identified as a candidate for therapeutic utility in the treatment of psoriasis.

Table 1 summarizes the results of these Northern hybridizations. TIG1 mRNA expression was clearly responsive to only a subset of retinoid inducers in this experimental system. Thus, detection of TIG1 mRNA induction provided a means for identifying the subset of retinoids that affected gene expression in cells that exhibit the psoriatic phenotype. The TIG1 hybridization probe, used under high stringency conditions, served as an instrument for detecting the TIG1 mRNA in these procedures.

TABLE 1

| Hybridization Assay for Retinoid Bioactivity: TIG1 mRNA Induction in Psoriatic Skin Rafts | | | |
|---|---|---|---|
| | Untreated | AGN-190168 | AGN-190299 |
| TIG1 mRNA Expression | (−) | (++++) | (++++) |

The specificity of the retinoid receptor(s) participating in the signal transduction pathway that leads to TIG1 mRNA expression was determined using a human keratinocyte model system. RNA samples isolated from keratinocytes stimulated with a variety of retinoid agonists were assayed for TIG1 mRNA induction according to the Northern blotting method described above. More specifically, primary human keratinocytes were treated for 24 hours with either RAR agonists AGN-190168, AGN-190121 [4-[4-(2,6,6-trimethyl-cyclohex-1-enyl) but-1-yne-3-enyl]-benzoic acid] and AGN-191183 [p-[(E)-2-(5,6,7,8-tetrahydro-5,5,8,8-tetramethyl-2-naphthyl)-prop-1-enyl] benzoic acid] or RXR agonists SR-11217 [1-(4-carboxyphenyl)-1-(7-(1,1,4,4-tetramethyl-1,2,3,4-tetrahydronaphthyl))-2-methylpropene] and SR-11237 [2-(5,6,7,8-tetrahydro-5,5,8,8-tetramethyl naphthalen-2-yl)-2-(4-carboxyphenyl)-1,3-dioxolane]. As summarized in Table 2, all of the RAR-specific retinoids used in the procedure induced TIG1 expression. In contrast, neither of the RXR-specific retinoids led to TIG1 mRNA induction. These results provided strong evidence that TIG1 mRNA induction was mediated through RAR-specific, but not RXR-specific, signal transduction pathways.

TABLE 2

Hybridization Assay for Retinoid Bioactivity:
TIG1 mRNA Induction in Keratinocytes

|  | Untreated | AGN-190168 | AGN-190121 | AGN-191183 | SR-11217 | SR-11237 |
|---|---|---|---|---|---|---|
| TIG1 mRNA Expression | (−) | (+) | (+) | (+) | (−) | (−) |

A key advantage underlying use of the TIG1 probe in assays to detect retinoid activity relates to enhanced sensitivity in both normal and psoriatic contexts. For example, the results from a test conducted according to the method of Example 6 indicated the TIG1 mRNA hybridization signal increased 16 fold after AGN-190168 stimulation. The CRABP II signal increased by only 5 fold under identical conditions. Thus, induction of the TIG1 mRNA can advantageously serve as a sensitive indicator of retinoid activity in cells exhibiting either normal or psoriatic phenotypes.

PCR-based assays for TIG1 mRNA induction represent alternative approaches for detecting retinoid bioactivity. The extraordinary sensitivity of the PCR technique results from the fact that the quantity of a polynucleotide sequence can be amplified more than a million fold by repetitive cycles of DNA synthesis. By selecting a set of primers that can be used to amplify a second polynucleotide sequence that corresponds to a constitutively expressed mRNA, results can effectively be normalized between two different reactions. This normalization allows for a relative quantitation of the amount of starting material present in different samples. In the exemplary procedure described below, two oligonucleotide primers for use in RT-PCR protocols were designed based on the sequence of the TIG1 cDNA. Other primer sets based on the TIG1 cDNA sequence and selected using standard criteria readily appreciated by those of ordinary skill in the art can also be used to detect TIG1 mRNA expression. Indeed, any oligonucleotide primer set that can be used to uniquely amplify a segment of the TIG1 cDNA in a PCR procedure are anticipated for use in assays for detecting TIG1 mRNA induction, for example by retinoids. Additionally, the assay can be modified by substituting skin-derived fibroblasts or normal or psoriatic skin raft cultures or keratinocytes as described below.

Example 11 describes a PCR-based assay for detecting TIG1 mRNA induction. The assay is useful for identifying retinoids having bioactivity in a variety of experimental systems.

EXAMPLE 11

PCR-Based Assay for Induction of the TIG1 mRNA by Retinoids in Keratinocytes

Cultured keratinocytes were treated with AGN-190168 at a concentration of 1 µM for 24 hours. Total RNA was prepared from mock-treated or AGN-190168 treated keratinocytes according to a standard guanidine thiocyanate procedure using materials purchased as a kit from Promega. RNA samples (1 µg) were reverse transcribed and PCR amplified using materials purchased as a kit from Perkin Elmer (Norwalk, Conn.). The TIG1 mRNA was amplified using synthetic DNA oligonucleotide primers having nucleotide sequences 5'-TCAGGTTTTTCTTACCCACTG-3' (SEQ ID NO:2) and 5'-ACCTGCTTTACAAGCAAATGA-3' (SEQ ID NO:3). The GAPDH mRNA was similarly reverse transcribed and PCR amplified using DNA oligonucleotide primers purchased from Stratagene (La Jolla, Calif.). Temperature cycling conditions employed in the procedure were: 94° C. for 30 seconds, 55° C. for 30 seconds, 72° C. for 1 minute. Aliquots of the reaction mixtures were removed as time points after every 3 cycles between 12 and 36 cycles, electrophoresed on a 2% agarose gel, stained with ethidium bromide and illuminated with ultraviolet light to visualize amplified DNA fragments.

Results indicated that RNA isolated from control and AGN-190168 induced keratinocytes, when used as a template in the RT-PCR protocol, gave rise to a specific amplification product of 211 bp in length. The intensity of the stained GAPDH fragments for each time point were roughly similar for both RNA samples. Thus, the GAPDH amplification product was used as a normalization standard to correct for differences between the amounts of starting material present in different RNA samples. The amount of GAPDH amplification product for any sample was proportional to the total quantity of RNA present in the starting sample. We note that other constitutively expressed mRNAs could be substituted for GAPDH mRNA as normalization standards with equally good results. A single band corresponding to the GAPDH amplification product was first observed after 15 PCR cycles when control cell RNA was used as a template, and after 18 cycles when RNA from AGN-190168 treated cells was used. This result indicated that a slightly greater quantity of RNA was present in the sample of control cell RNA compared to AGN-190168 induced cell RNA. In spite of this, no TIG1 amplification product could be detected when control cell RNA was used as a template. Conversely, a unique amplification product was easily observed after 24 PCR cycles when AGN-190168 induced cell RNA was used as a template. This clearly demonstrated that the AGN-190168 induced TIG1 mRNA could be detected in a PCR-based protocol. This result also demonstrated that the PCR assay could discriminate between basal and induced expression of the TIG1 mRNA. No TIG1 amplification product was detected in RNA samples from control cells. Conversely, a DNA fragment was clearly amplified when RNA from AGN-190168 induced cells was used as a template in the procedure. This confirmed the utility of the PCR assay for detecting induction of the TIG1 mRNA.

Assays that detect induced TIG1 mRNA expression as an indicator of retinoid bioactivity can employ a variety of nucleic acid probes based on the sequence of the TIG1 cDNA disclosed herein. In particular, any probe having a polynucleotide sequence that can hybridize the sense strand of the TIG1 cDNA under high stringency conditions, but not to mRNA isolated from untreated skin-derived cells is anticipated for use in detecting the TIG1 mRNA in solution or blot hybridization protocols. Further, any set of oligonucleotide primers that can be used to amplify TIG1 polynucleotide sequences starting with a TIG1 mRNA template is also anticipated for use in assays for retinoid bioactivity according to the PCR-based method of our invention.

Two different approaches can be used to determine the hybridization characteristics of nucleic acid probes useful in the practice of the present invention. These approaches can be classified as "theoretical" and "emperical." Descriptions of the theoretical and emperical approaches for determining the melting temperatures of nucleic acid probes can be found in *Molecular Cloning: A Laboratory Manual* (Sambrook et al. eds. Cold Spring Harbor Lab Publ. 1989) on pages 11.46 and 11.55, respectively. These methods can be used to identify oligonucleotide primers for use in primer extension and PCR protocols, as well as hybridization probes for use in blotting protocols.

We also contemplate the use of reporter gene assays to identify retinoids that, like AGN-190168, activate TIG1 gene expression. As used herein, a "reporter gene" is a gene that encodes a "reporter" molecule. A "reporter" can be any molecule that can be detected in cells carrying the corresponding "reporter gene," but not in cells lacking that reporter gene. Thus, for example, a reporter can be an enzyme, a colored or fluorescent product, or an antigen that can be detected by antibodies. Reporter gene assays are ideally suited to study the activity of genes that are regulated at the transcriptional level.

The product of a reporter gene is useful in the study of gene regulation. The protein encoded by a reporter gene can also be employed as a surrogate for detecting the products of a different gene. Accordingly, reporter genes can advantageously serve as indirect indicators of gene activity when the reporter is more easily assayed than the product of the gene of interest. In cases where it is desirable to measure the activity of a weakly expressed gene, or the product of a gene for which an assay is not available, a molecular genetic construct that allows the reporter to be expressed in place of the gene of interest can facilitate such measurements. A protein product is commonly the object of the reporter assay.

Useful reporter molecules may function either as enzymes or as ligands that can be detected by tagged antibodies or other ligand-binding molecules. Specific examples of reporters that are useful in the study of gene regulation include bacterial genes such as those encoding chloramphenicol acetyltransferase (CAT) and beta-galactosidase (β-gal), and the firefly luciferase gene. The protein products of all three of these reporters can easily be detected by means of simple and sensitive enzymatic assays. In addition to reporters that are detected by virtue of their enzymatic activities, other reporters can be detected by antibody-based assays.

The Example presented below illustrates one approach that can be used to obtain genomic clones by a standard library screening protocol. As will be recognized by those having ordinary skill in the art, PCR-based techniques provide an alternative method of isolating the TIG1 promoter.

Example 12 illustrates one technique that can be used to isolate the transcription control region of the TIG1 gene.

EXAMPLE 12

Isolation of the TIG1 Promoter

A nucleic acid segment corresponding to the 5' end of the TIG1 cDNA is first identified for use as a nucleic acid probe according to standard criteria. This polynucleotide is then radiolabeled to high specific activity and used as a hybridization probe to identify recombinant clones harboring the 5' region of the TIG1 cDNA. Some of the genomic clones will also harbor the TIG1 promoter. The transcription initiation site is identified by S1 nuclease mapping or primer extension analysis. The polynucleotide region upstream of the transcription initiation site will possess cis-regulatory elements that confer inducibility of TIG1 downstream sequences by retinoids such as AGN-190168.

A reporter gene construct is prepared by ligating the TIG1 transcription control region upstream of a reporter gene. Plasmid vectors appropriate for this purpose can be commercially obtained. For example, the pGL-BASIC vector (Promega) is a vector that harbors the firefly luciferase coding sequence. This vector would be an appropriate recipient of the TIG1 promoter according to the contemplated method.

With the availability of reporter constructs as described above, it becomes possible to create assays for compounds that induce the TIG1 promoter.

Example 13 illustrates how reporter gene constructs can be used in sensitive assays to identify retinoids that activate the TIG1 promoter.

EXAMPLE 13

Use of TIG1 Reporter Gene Constructs in Assays to Identify Retinoids that Stimulate TIG1 Transcription Stable transfectants harboring the TIG1 promoter/luciferase expression construct of Example 12 are propagated under standard conditions. A culture of the cells is split into four equal parts, and propagated in separate flasks. The first flask is left as an untreated control. A second flask is treated with AGN-190168 as a positive control for induction of the expression construct. The third and fourth flasks are treated with test retinoids "A" and "B." At the end of the treatment period, cells from each of the cultures are harvested and used to prepare cytoplasmic extracts. Luciferase assays are performed using aliquots of each of the four extracts according to standard protocols. The extract from uninduced cells contains a very low level of luciferase activity, while the extract prepared from AGN-190168 treated cells has a very high level of activity. These results from the control extracts confirm that AGN-190168 induces the TIG1 promoter. The extract of cells induced with retinoid "A" has a level activity similar to the uninduced control extract. This result indicates that retinoid "A" does not exhibit bioactivity in the reporter assay. The extract of cells induced with retinoid "B" has a level of luciferase activity comparable to the AGN-190168 treated cell extract. Retinoid "A" exhibits bioactivity in the reporter assay.

In addition to assays based on detection of the TIG1 mRNA or reporter molecules, other assays based on retinoid-dependent cell survival are also contemplated. The approach employed in such assays relies on expression of a selectable marker under transcriptional control of the TIG1 promoter. For example, we contemplate stable cell lines transfected with DNA constructs having the bacterial neomycin drug resistance gene operationally linked to the TIG1 promoter. High level expression of the drug resistance marker will depend on activation of the TIG1 promoter. In the absence of the inducer but in the presence of the drug G418, no cell growth will occur. Conversely, in the presence of an inducer of the TIG1 promoter, high level expression of the neomycin resistance gene will permit cell survival in the presence of G418. Accordingly, retinoids that activate the TIG1 promoter will be identified by virtue of their ability to promote cell survival under drug selection.

Bioactive compounds found to induce TIG1 gene expression will be identified as having potential as therapeutic drugs. The identification of such bioactive compounds can be made according to assays that detect induced expression of the TIG1 mRNA or a reporter gene under transcriptional control of the TIG1 promoter. Alternatively, assays based on induction of the TIG1 protein or on cell survival assays as disclosed above can also be used to identify such compounds. The following Example describes a procedure that can be used to investigate the therapeutic potential of the bioactive compounds, such as AGN-190299.

Example 14 illustrates how bioactive compounds identified according to the methods described herein will be tested for therapeutic value in the treatment of psoriasis. A topical administration protocol is described below.

EXAMPLE 14

Assessing the Therapeutic Potential of Compounds that Stimulate TIG1 Expression A population of adult volunteers having large psoriatic plaques is first identified and then randomly divided into two groups. One group is a control group to be treated with a placebo while the other (test) group is to be treated with a composition containing a bioactive retinoid. The treatment protocol and assessment of drug efficacy is performed essentially as described by Esgleyes-Ribot et al., in the *Journal of the American Academy of Dermatology* 30:581 (1994).

A compound that induces TIG1 gene expression is identified according to methods such as those disclosed above. This compound is then combined into a cream comprising a pharmaceutically acceptable carrier and 0.05% of the bioactive retinoid. The cream is formulated using materials and methods familiar to one having ordinary skill in the art. A placebo consists of the carrier alone and does not contain any retinoid.

Participants in the experimental protocol are appropriately treated either with the placebo or with the cream containing the retinoid to be tested for therapeutic potential. The psoriatic plaques of individuals in the control group are treated with the placebo twice daily for a period of two weeks. Similarly, the psoriatic plaques of individuals in the test group are treated with the composition containing bioactive retinoid twice daily for the same period.

Individuals administered with the bioactive retinoid show clinical improvement after the first two weeks of treatment. In this context, clinical improvement is assessed by erythema, induration and scaling. Immunohistochemical analysis of standard markers indicates that normalization of skin histology parallels the clinical improvement observed in lesions treated with the composition containing the bioactive retinoid. Similarly, expression of inflammatory markers is reduced in biopsies obtained from lesions treated with the composition containing the bioactive retinoid. Few if any members of the control group show clinical improvement. These findings indicate the bioactive retinoid is effective as a psoriasis treatment, and that treatment of psoriatic lesions with the placebo alone had no beneficial effect.

The novel TIG1 cDNA described above was induced by an RAR-$\beta$/RAR-$\gamma$ selective synthetic retinoid both in primary cultured skin cells and in psoriatic lesions. Since the TIG1 protein exhibits structural features characteristic of a transmembrane protein, we anticipate its possible role as a cell adhesion molecule. Conceivably, cell surface expression of the TIG1 protein could promote cell—cell contact, ultimately leading to reduced keratinocyte proliferation. Further, the TIG1 mRNA was not induced by RXR-specific retinoids. In contrast, it was induced by all RAR-specific synthetic retinoids tested in our experiments.

Unlike the TIG1 gene, the CRABP II gene responds both to RARs and RXRs (Nagpal, et al. *Cell* 70:1007 (1992)) and contains a complex retinoid responsive element consisting of a DR1 and a DR2 repeats (Durand, et al. *Cell* 71:73 (1992)). Mangelsdorf et al. (The Retinoids: Biology, Chemistry, and Medicine, M. B. Sporn, A. B. Roberts and D. S. Goodman, eds. (New York: Raven Press, Ltd. (1994)) have disclosed that the DR1 element responds to RXRs and the DR2 element responds primarily to RARs.

Whereas Elder, et al. (*J. Invest. Dermatol.* 100:356 (1993)) disclosed that the CRABP II gene is responsive to RA in normal human skin, Didierjean, et al. (*Biochem. Biophys. Res. Commun.* 180:204 (1991)) had earlier demonstrated that CRABP II is constitutively expressed at high levels in psoriatic skin. Elder et al. (*J. Toxicol.—Cut. & Ocular Toxicol.* 12:173 (1993)) disclosed that CRABP II was down-regulated by RA in submerged keratinocyte cultures. In contrast, TIG1 was not significantly expressed in untreated non-lesional skin and was induced in primary submerged keratinocyte cultures in a retinoid-dependent manner. Thus, TIG1 represents a superior indicator gene for monitoring the bioactivity of retinoids in skin and cultures of skin-derived cells.

---

We claim:

1. An isolated polynucleotide having a sequence complementary to the sequence of SEQ ID NO: 4 wherein said polynucleotide sequence specifically hybridizes to Tazarotene Inducible Gene (TIG1) under high stringency conditions (0.1×SSPE/1% SDS at 65 C).

2. The polynucleotide of claim 1 hybridized to a second polynucleotide to form a double-stranded polynucleotide, said second polynucleotide having the sequence of SEQ ID NO: 4.

3. A method for identifying a compound to be tested for treatment of psoriasis, comprising the following steps:
(a) obtaining a negative control sample containing RNA isolated from an untreated control culture of cells derived from skin;
(b) obtaining a test sample containing RNA isolated from a test culture of cells derived from skin, wherein said test culture has been treated with said test compound;
(c) quantitating the amount of Tazarotene Inducible Gene-1 (TIG1) RNA present in said negative control sample and said test sample, said TIG1 RNA being an RNA having a polynucleotide sequence corresponding to the sequence of SEQ ID NO: 4;
(d) comparing the amount of TIG1 RNA in said negative control sample and said test sample to determine if the amount of TIG1 RNA in said test sample is greater or lesser than the amount of TIG1 RNA in said negative control sample, wherein said test compound is identified for the treatment of psoriasis if the amount of TIG1 RNA in said test sample is greater than five-fold more than the amount of TIG1 RNA in said negative control sample.

4. The method of claim 3, wherein quantitating step (c) comprises:
(i) hybridizing with said negative control sample and said test sample a labeled probe having a sufficient number of consecutive nucleotides complementary to the sequence of SEQ ID NO:4 to specifically hybridize with TIG1 mRNA under high stringency conditions (0.1×SSPE/1% SDS at 65° C.); and (ii) quantitating the amount of hybridization between said probe and each of said samples.

5. The method of claim 3, wherein the negative control sample is derived from keratinocytes or fibroblasts.

6. The method of claim 4, wherein said probe is labeled with a radioactive label.

7. The method of claim 6, wherein step (ii) comprises autoradiography.

8. The method of claim 4, wherein the RNA contained in said negative control sample and the RNA contained in said test sample are immobilized to a solid support prior to hybridizing step (i).

9. The method of claim 3, wherein quantitating step (c) comprises:

(i) reverse transcribing mRNA present in said negative control samples and said test samples, wherein product of reverse transcription is a polynucleotide sequence having a sequence which is identical to at least part of the sequence of SEQ ID NO:4, said product being TIG cDNA, and wherein said polynucleotide specifically hybridizes to Tazarotene Inducible Gene (TIG1) under high stringency conditions (0.1×SSPE/1% SDS at 65° C.), (ii) amplifying specifically any TIG1 cDNA produced in step (i) by a polymerase chain reaction, said polymerase chain reaction producing TIG1 amplification products; and (iii) quantitating said TIG1 amplification products produced when negative control and test samples are used as sources of RNA templates for reverse transcribing step (i).

10. The method of claim 9, further comprising normalizing the results of step (iii) to the amount of a constitutively expressed mRNA present in both said negative control sample and said test sample.

11. The method of claim 9, wherein DNA oligonucleotides having the sequences of SEQ ID NO:2 and SEQ ID NO:3 are primers in the polymerase chain reaction of amplifying step (ii).

12. The method of claim 3, wherein the quantitating step comprises a nuclease protection assay.

13. The method of claim 3, wherein quantitating step (c) comprises:

(i) hybridizing with nucleic acids in said negative control sample and said test sample a DNA primer complementary to a segment of a polynucleotide having the sequence of SEQ ID NO:4 to result in a hybridized primer, said primer having a label;

(ii) extending the primer hybridized in step (i) by the activity of a reverse transcriptase enzyme to produce cDNA;

(iii) quantitating the amount of labeled cDNA produced in extending step (ii), wherein the cDNA quantitated has a length which corresponds to the number of nucleotides between the 5' end of said hybridized primer and the 5' terminus of the TIG1 mRNA.

14. The method of claim 13, wherein the primer is labeled at its 5' end.

15. The method of claim 12 which comprises the following steps:

i) hybridizing with nucleic acids in said negative control sample and said test sample a single stranded polynucleotide probe, said probe having a sequence complementary to a segment of the sequence of SEQ ID NO: 4 linked to a contiguous stretch of nucleotides not complementary to the sequence of SEQ ID NO: 4, said complementary sequence sufficient in length to hybridize specifically to TIG1 mRNA in an aqueous buffer made 80% formamide;

ii) digesting products of hybridizing step (i) with a single-strand-specific nuclease;

iii) separating products of digesting step (ii) by electrophoresis;

iv) quantitating the amount of undigested probe remaining after digesting step(ii) wherein the undigested probe quantitated has a length which corresponds to the sequence of said single-stranded polynucleotide probe which is complementary to the sequence of SEQ ID NO: 4.

16. The method of claim 3, wherein the skin of steps (a) and (b) is psoriatic.

17. The method of claim 3, wherein the skin of steps (a) and (b) is nonpsoriatic.

18. The method of claim 15, wherein said enzyme is S1 nuclease or RNase.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

GCGGCCGCCC TTTTTTTTT TTTTT  25

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

TCAGGTTTTT CTTACCCACT G  21

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

ACCTGCTTTA CAAGCAAATG A  21

( 2 ) INFORMATION FOR SEQ ID NO:4:

( i ) SEQUENCE CHARACTERISTICS:
        ( A ) LENGTH: 862 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Coding Sequence
        ( B ) LOCATION: 37...720

5,650,279

( D ) OTHER INFORMATION:

( x i ) SEQUENCE DESCRIPTION: SEQ ID NO:4:

| | | | | | | | | | | | | | | | | |
|---|---|---|---|---|---|---|---|---|---|---|---|---|---|---|---|---|
| CCACGTCCGG | GGTGCCGAGC | CAACTTTCCT | GCGTCC | ATG | CAG | CCC | CGC | CGG | CAA | | | | | | | 54 |
| | | | | Met 1 | Gln | Pro | Arg | Arg 5 | Gln | | | | | | | |
| CGG | CTG | CCC | GCT | CCC | TGG | TCC | GGG | CCC | AGG | GGC | CCG | CGC | CCC | ACC | GCC | 102 |
| Arg | Leu | Pro | Ala 10 | Pro | Trp | Ser | Gly | Pro 15 | Arg | Gly | Pro | Arg | Pro 20 | Thr | Ala | |
| CCG | CTG | CTC | GCG | CTG | CTG | CTG | TTG | CTC | GCC | CCG | GTG | GCG | GCG | CCC | GCG | 150 |
| Pro | Leu | Leu 25 | Ala | Leu | Leu | Leu 30 | Leu | Leu | Ala | Pro | Val | Ala 35 | Ala | Pro | Ala | |
| GGG | TCC | GGG | GGC | CCC | GAC | GAC | CCT | GGG | CAG | CCT | CAG | GAT | GCT | GGG | GTC | 198 |
| Gly | Ser 40 | Gly | Gly | Pro | Asp | Asp 45 | Pro | Gly | Gln | Pro | Gln 50 | Asp | Ala | Gly | Val | |
| CCG | CGC | AGG | CTC | CTG | CAG | CAG | GCG | GTG | CGC | GCG | GCG | CTT | CAC | TTC | TTC | 246 |
| Pro 55 | Arg | Arg | Leu | Leu | Gln 60 | Gln | Ala | Val | Arg | Ala 65 | Ala | Leu | His | Phe | Phe 70 | |
| AAC | TTC | CGG | TCC | GGC | TCG | CCC | AGC | GCG | CTG | CGA | GTG | CTG | GCC | GAG | GTG | 294 |
| Asn | Phe | Arg | Ser | Gly 75 | Ser | Pro | Ser | Ala | Leu 80 | Arg | Val | Leu | Ala | Glu 85 | Val | |
| CAG | GAG | GGC | CGC | GCG | TGG | ATT | AAT | CCA | AAA | GAG | GGA | TGT | AAA | GTT | CAC | 342 |
| Gln | Glu | Gly | Arg 90 | Ala | Trp | Ile | Asn | Pro 95 | Lys | Glu | Gly | Cys | Lys 100 | Val | His | |
| GTG | GTC | TTC | AGC | ACA | GAG | CGC | TAC | AAC | CCA | GAG | TCT | TTA | CTT | CAG | GAA | 390 |
| Val | Val | Phe 105 | Ser | Thr | Glu | Arg | Tyr 110 | Asn | Pro | Glu | Ser | Leu 115 | Leu | Gln | Glu | |
| GGT | GAG | GGA | CGT | TTG | GGG | AAA | TGT | TCT | GCT | CGA | GTG | TTT | TTC | AAG | AAT | 438 |
| Gly | Glu | Gly 120 | Arg | Leu | Gly | Lys | Cys 125 | Ser | Ala | Arg | Val | Phe 130 | Phe | Lys | Asn | |
| CAG | AAA | CCC | AGA | CCA | ACC | ATC | AAT | GTA | ACT | TGT | ACA | CGG | CTC | ATC | GAG | 486 |
| Gln 135 | Lys | Pro | Arg | Pro | Thr 140 | Ile | Asn | Val | Thr | Cys 145 | Thr | Arg | Leu | Ile | Glu 150 | |
| AAA | AAG | AAA | AGA | CAA | CAA | GAG | GAT | TAC | CTG | CTT | TAC | AAG | CAA | ATG | AAG | 534 |
| Lys | Lys | Lys | Arg | Gln 155 | Gln | Glu | Asp | Tyr | Leu 160 | Leu | Tyr | Lys | Gln | Met 165 | Lys | |
| CAA | CTG | AAA | AAC | CCC | TTG | GAA | ATA | GTC | AGC | ATA | CCT | GAT | AAT | CAT | GGA | 582 |
| Gln | Leu | Lys 170 | Asn | Pro | Leu | Glu | Ile 175 | Val | Ser | Ile | Pro | Asp 180 | Asn | His | Gly | |
| CAT | ATT | GAT | CCC | TCT | CTG | AGA | CTC | ATC | TGG | GAT | TTG | GCT | TTC | CTT | GGA | 630 |
| His | Ile | Asp 185 | Pro | Ser | Leu | Arg | Leu 190 | Ile | Trp | Asp | Leu | Ala 195 | Phe | Leu | Gly | |
| AGC | TCT | TAC | GTG | ATG | TGG | GAA | ATG | ACA | ACA | CAG | GTG | TCA | CAC | TAC | TAC | 678 |
| Ser | Ser | Tyr 200 | Val | Met | Trp | Glu | Met 205 | Thr | Thr | Gln | Val | Ser 210 | His | Tyr | Tyr | |
| TTG | GCA | CAG | CTC | ACT | AGT | GTG | AGG | CAG | TGG | GTA | AGA | AAA | ACC | TGAAAATTAA | | 730 |
| Leu 215 | Ala | Gln | Leu | Thr | Ser 220 | Val | Arg | Gln | Trp | Val 225 | Arg | Lys | Thr | | | |
| CTTGTGCCAC | AAGAGTTACA | ATCAAAGTGG | TCTCCTTAGA | CTGAATTCAT | GTGAACTTCT | | | | | | | | | | | 790 |
| AATTTCATAT | CAAGAGTTGT | AATCACATTT | ATTTCAATAA | ATATGTGAGT | TCCTGCAAAA | | | | | | | | | | | 850 |
| AAAAAAAAAA | AA | | | | | | | | | | | | | | | 862 |

( 2 ) INFORMATION FOR SEQ ID NO:5:

( i ) SEQUENCE CHARACTERISTICS:
        ( A ) LENGTH: 228 amino acids
        ( B ) TYPE: amino acids
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:5:

```
Met Gln Pro Arg Arg Gln Arg Leu Pro Ala Pro Trp Ser Gly Pro Arg
 1               5                  10                  15
Gly Pro Arg Pro Thr Ala Pro Leu Leu Ala Leu Leu Leu Leu Leu Ala
            20                  25                  30
Pro Val Ala Ala Pro Ala Gly Ser Gly Gly Pro Asp Asp Pro Gly Gln
        35                  40                  45
Pro Gln Asp Ala Gly Val Pro Arg Arg Leu Leu Gln Gln Ala Val Arg
    50                  55                  60
Ala Ala Leu His Phe Phe Asn Phe Arg Ser Gly Ser Pro Ser Ala Leu
65                  70                  75                  80
Arg Val Leu Ala Glu Val Gln Glu Gly Arg Ala Trp Ile Asn Pro Lys
                85                  90                  95
Glu Gly Cys Lys Val His Val Val Phe Ser Thr Glu Arg Tyr Asn Pro
            100                 105                 110
Glu Ser Leu Leu Gln Glu Gly Glu Gly Arg Leu Gly Lys Cys Ser Ala
            115                 120                 125
Arg Val Phe Phe Lys Asn Gln Lys Pro Arg Pro Thr Ile Asn Val Thr
    130                 135                 140
Cys Thr Arg Leu Ile Glu Lys Lys Lys Arg Gln Gln Glu Asp Tyr Leu
145                 150                 155                 160
Leu Tyr Lys Gln Met Lys Gln Leu Lys Asn Pro Leu Glu Ile Val Ser
                165                 170                 175
Ile Pro Asp Asn His Gly His Ile Asp Pro Ser Leu Arg Leu Ile Trp
            180                 185                 190
Asp Leu Ala Phe Leu Gly Ser Ser Tyr Val Met Trp Glu Met Thr Thr
        195                 200                 205
Gln Val Ser His Tyr Tyr Leu Ala Gln Leu Thr Ser Val Arg Gln Trp
    210                 215                 220
Val Arg Lys Thr
225
```